United States Patent [19]

Habermann

[11] Patent Number: 4,772,750

[45] Date of Patent: Sep. 20, 1988

[54] METHOD OF PRODUCING AMINES

[75] Inventor: Clarence E. Habermann, Midland, Mich.

[73] Assignee: The Dow Chemical Company, Midland, Mich.

[21] Appl. No.: 914,960

[22] Filed: Oct. 3, 1986

Related U.S. Application Data

[63] Continuation-in-part of Ser. No. 744,837, Jun. 14, 1985, abandoned.

[51] Int. Cl.$^4$ .................... C07C 85/08; C07C 85/04
[52] U.S. Cl. .................... 564/472; 564/398; 564/402; 564/446; 564/447; 564/473; 564/480
[58] Field of Search ............ 564/480, 472, 473, 398, 564/402, 446, 447

[56] References Cited

U.S. PATENT DOCUMENTS

| | | | |
|---|---|---|---|
| 2,696,475 | 12/1954 | Farrow | 252/463 |
| 2,861,995 | 11/1958 | MacKenzie | 260/268 |
| 3,037,023 | 5/1962 | Moss et al. | 260/268 |
| 3,151,113 | 9/1964 | Advani et al. | 260/247 |
| 3,347,926 | 10/1967 | Zech | 260/585 |
| 3,520,933 | 7/1970 | Adam et al. | 260/585 |
| 3,637,895 | 1/1972 | Riegel et al. | 502/224 |
| 3,654,370 | 4/1972 | Yeskey | 260/584 B |
| 3,721,632 | 3/1973 | Miller et al. | 502/225 |
| 3,808,152 | 4/1974 | Nagase et al. | 252/463 X |
| 3,922,303 | 11/1975 | Takehara et al. | 260/570.5 R |
| 4,014,933 | 3/1977 | Boettger et al. | 260/563 R |
| 4,036,883 | 7/1977 | Voges et al. | 260/585 B |
| 4,111,840 | 9/1978 | Best | 252/432 |
| 4,152,353 | 5/1979 | Habermann | 260/585 B |
| 4,153,581 | 5/1979 | Habermann | 252/472 |
| 4,209,424 | 6/1980 | Le Goff et al. | 252/474 |
| 4,254,060 | 3/1981 | Kimura et al. | 564/479 |
| 4,255,357 | 3/1981 | Gardner et al. | 564/480 |
| 4,272,455 | 6/1981 | Cook et al. | 564/503 |
| 4,308,176 | 12/1981 | Kristiansen | 252/463 |
| 4,362,655 | 12/1982 | Jenkins | 252/474 |
| 4,409,399 | 10/1983 | Swift et al. | 564/473 |
| 4,637,820 | 1/1972 | Dodman et al. | 564/416 |

OTHER PUBLICATIONS

Derwent 65653D, (1976).
Chemical Abstracts 77:74890b, (vol. 77), 1972.
Chemical Abstracts 80:59430V, (vol. 80), 1974.
Derwent 01016Y, (1976).

*Primary Examiner*—Charles F. Warren
*Assistant Examiner*—Elizabeth A. Hanley

[57] ABSTRACT

A method for producing amines, the method comprising contacting at reactive conditions at least one alcohol, aldehyde or ketone, or a mixture thereof, with an aminating agent in the presence of a cobalt/copper catalyst, is improved by employing as the catalyst a composition comprising cobalt and copper, the catalyst being prepared by the molten salt impregnation technique.

9 Claims, No Drawings

METHOD OF PRODUCING AMINES

This is a continuation of application Ser. No. 744,837 filed June 14, 1985, now abandoned.

BACKGROUND OF THE INVENTION

The present invention relates to an improved method of producing amines from alcohols, aldehydes, ketones, and mixtures thereof. In one aspect, the invention relates to an ammonolytic method while in another aspect it relates to a catalyst useful therein.

The amination of alcohols, aldehydes, and ketones using catalysts containing nickel, copper or both is known. For example, see U.S. Pat. Nos. 4,153,581; 4,409,399; 4,152,353 and the patents cited therein.

Nickel-containing amination catalysts have been prepared using molten salt impregnation methods. U.S. Pat. No. 4,209,424 discloses amination catalysts containing at least one metal from the group consisting of nickel, cobalt, and copper. Example 12 of said patent teaches using molten nickel nitrate to prepare a nickel on alumina catalyst. The catalyst of Example 12 has relatively low amination activity. Similarly, U.S. Pat. No. 2,696,475 teaches the preparation of supported reduction catalysts which contain nickel, cobalt and/or copper. Said patent teaches that the use of solutions is better than the use of molten salts to give a catalyst with the greatest activity per weight of metal.

Heretofore, a cobalt/copper amination catalyst prepared using the fused salt impregnation technique, and having increased amination activity as compared to cobalt/copper amination catalysts prepared via aqueous impregnation, has not been disclosed.

SUMMARY OF THE INVENTION

According to the present invention, a method of producing amines, the method comprising contacting at reactive conditions at least one alcohol, ketone, or aldehyde with an aminating agent in the presence of a cobalt/copper ammonolytic catalyst, is surprisingly improved by using as the catalyst a composition comprising cobalt and copper, the catalyst being prepared by the molten salt impregnation technique. These compositions demonstrate comparable or superior ammonolytic activity as compared to cobalt/copper catalysts prepared using aqueous impregnation techniques.

DETAILED DESCRIPTION OF THE INVENTION

The catalytic compositions of the present invention comprise cobalt and copper, and, optionally, at least one other catalytic material. These compositions are prepared using the molten salt impregnation technique, which is well-known. However, for the purposes of the present invention, the term "molten salt impregnation technique" refers to said technique wherein the preparation does not include washing the impregnated support before calcination.

The preparation of a catalyst of the present invention generally involves contacting a support with molten salts of the desired catalytic metals, filtering and drying the resulting impregnated support, and calcining the impregnated support. The drying step typically is done at an elevated temperature, e.g., 60° C.–180° C., and the dry composition is then decomposed at a temperature between about 200° C. and about 400° C. for a suitable period of time, e.g., 2 hours, to the corresponding oxides. Calcination typically is performed at a temperature sufficient to decompose the deposited salt mixture. However, the temperature preferably is chosen to avoid large decreases in catalyst surface area. The resulting oxide mixture is then reduced with hydrogen, sodium borohydride, hydrazine, a reducing metal of greater oxidation potential than cobalt, carbon monoxide or some other suitable reducing agent, such as the reaction mixture, i.e., the catalyst can be reduced in the reactor using the reactants. The degree of reduction is temperature dependent but generally the first two components (cobalt and copper) are reduced to the active metal while the optional component, e.g., zinc, iron, zirconium or a mixture thereof, remains an oxide. Typical reduction temperatures range from about 175° C. to about 400° C. When this reduction is with hydrogen, a temperature between about 150° C. and about 250° C. for about 6 to 7 hours is usually adequate. The reduced catalyst is thereafter generally handled in the absence of air. The time required for calcination, reduction and other preparative steps is dependent on temperature, as is well-known.

Examples of typical metal salt anions include organic salts, such as the acetates, formates, lactates, and the like, and inorganic salts such as the nitrates, chlorides, fluorides, borates, and sulfates, with the nitrates being preferred. Mixed metal salts or complexes can be employed if desired. The support impregnation can be carried out at any temperature at which the salt is molten. It is preferred to perform the impregnation at a temperature at which the salt is not decomposing.

The support can be selected from known catalytic supports, and typically is a refractory oxide. Examples of typical supports include alumina, silica, zirconia, clays, Kieselguhr, zeolites, silica gel, magnesia, zircon (a mixture of zirconia and silica), and the like. Mixtures of supports can be employed. The metal loading (on an oxide-free basis) usually is at least about 0.5 percent and is preferably at least about 10 percent of the total weight (support plus catalytic metals). The maximum catalytic metal content can vary to convenience.

The catalytic metal component of the catalyst of the present invention typically comprises (calculated on an oxide-free basis in mole percent): (1) from about 1 to about 95 percent cobalt; and (2) from about 8 to about 95 percent copper. Preferably, the catalyst is substantially free of nickel. Other catalytic or promoter metals can be present in an amount up to about 20 percent. Examples of typical additional catalytic or promoter metals include rhenium, chromium, iron, zinc, zirconium and mixtures thereof. Preferred additional metals are iron, zinc, zirconium and mixtures thereof. Preferred catalytic metal components comprise from about 5 to about 80 percent cobalt, from about 15 to about 60 percent copper, and from about 1 to about 15 percent of an additional catalytic component.

More preferred catalytic metal components comprise from about 6 to about 70 percent cobalt, from about 20 to about 50 percent copper, and from about 4 to about 10 percent of an additional catalytic component.

Compositions wherein the additional catalytic component comprises only iron, or only zinc or only zirconium, are preferred over compositions wherein the additional component comprises a mixture of these components. Compositions wherein the additional component comprises only zirconium are particularly preferred. The preferred amount of zirconium is from about 5 to about 6 percent.

A catalytic amount of the composition is required for the practice of this invention. The minimum amount of catalyst required will vary with the method reagents and conditions, but a typical minimum amount of about 0.1 weight percent, and preferably about 1 weight percent, based on the weight of the starting materials, is employed. Practical considerations, such as convenience, catalyst recovery, economy, etc., are the only limitations upon the maximum amount of catalyst that can be used.

Any alcohol that can be used in known ammonolytic methods can be used in the practice of this invention. These alcohols comprise a wide variety of hydroxy-containing materials. Representative alcohols include: primary and secondary alcohols, such as alkanols of 1 to about 18 carbon atoms, e.g., methanol, n-propanol, isopropanol, n-butanol, sec-butanol, isobutanol, pentanol, hexanol, 2-ethylhexanol, tridecanol, stearyl alcohol, etc.; cycloalkanols of 5 to 12 carbons atoms, e.g., cyclohexanol, cycloheptanol, etc.; aralkanols of 7 to about 40 carbon atoms, e.g., benzyl alcohol, 2-phenyl ethanol, etc.; polyhydric alcohols of 2 to about 15 carbon atoms, e.g., ethylene glycol, propylene glycol, 1,3-butanediol, 1,4-butanediol, 1,5-pentanediol hexamethylene glycol, decamethylene glycol, 1,12-dihydroxyoctadecane-glycerol, etc.; polymeric polyhydric alcohols, e.g., polyvinyl alcohol; glycol ethers and polyalkyene glycol ethers, e.g., methyl glycol, ethyl glycol, butyl glycol, diethylene glycol, triethylene glycol, tetraethylene glycol, higher polyethylene glycols, dipropylene glycol, tripropylene glycol, polypropylene glycol ether, polybutylene glycol ether, etc.; aminated alcohols, such as alkanolamines, e.g., ethanolamine, propanolamine, isopropanolamine, hexanolamine, diethanolamine, diisopropanolamine, dimethylethanolamine, etc.; and aminated polyhydric alcohols and glycol ethers, e.g., aminated polyethylene glycol, etc. Other suitable hydroxy-containing compounds are disclosed in U.S. Pat. Nos. 3,347,926, 3,654,370 and 4,014,933.

Any aldehyde or ketone that can be produced from the dehydrogenation of the alcohols here used can also be used in the practice of this invention. Representative aldehydes include: methanal, ethanal, propanal, butanal, cyclohexanal, benzylaldehyde, and aldehydes prepared from the dehydrogenation of polyhydric alcohols, polymeric polyhydric alcohols, glycol ethers and polyalkylene glycol ethers, aminated alcohols, aminated polyhydric alcohols and glycol ethers, etc. Representative ketones include: propanone, butanone, 2-pentanone, 3-pentanone, 3-methyl-2-butanone, 1-phenyl-2-propanone, acetophenone, n-butyrophenone, benzophenone, 3-nitro-4'-methylbenzophenone and ketones prepared from the dehydrogenation of polyhydric alcohols, polymeric polyhydric alcohols, glycol ethers and polyalkylene glycol ethers, aminated alcohols, aminated polyhydric alcohols and glycol ethers, etc.

As used herein, "at least one alcohol, aldehyde or ketone, or a mixture thereof," means that these compounds can be used either singly (which is preferred), i.e., only one alcohol, only one aldehyde or only one ketone, or in a mixture comprising a combination of these compounds, e.g., a mixture of two or more alcohols, or two or more aldehydes, or two or more ketones, or of at least one alcohol and at least one aldehyde, or of at least one aldehyde and at least one ketone, or of at least one alcohol and at least one ketone, or of at least one alcohol, at least one aldehyde and at least one ketone.

The term "alcohol" includes those compounds containing both a hydroxy function and a carbonyl function and the term "aldehyde" includes those compounds without a hydroxy function but containing both an aldehyde carbonyl and a ketone carbonyl. Aldehydes are preferred to ketones and alcohols are preferred to aldehydes.

The aminating agents of this invention are ammonia or primary or secondary amines. The primary and secondary amines generally have alkyl radicals of 1 to about 12 carbon atoms or cycloalkyl radicals of 5 to 8 carbon atoms or aralkyl radicals of 7 to about 40 carbon atoms and include such compounds as: methylamine, dimethylamine, ethylamine, diethylamine, isopropylamine, n-butylamine, sec-butylamine, isobutylamine, ethylenediamine, benzylamine, cyclohexylamine, aniline, etc. Other suitable amines include cyclic amines which can contain hetero atoms other than nitrogen, such as oxygen, and these compounds include: morpholine, pyrrolidine, piperidine, piperazine, etc. When ammonia is the aminating agent, primary amines are obtained; when a primary amine is the aminating agent, secondary amines are obtained; when a secondary amine is the aminating agent, tertiary amines are obtained. These aminating agents, like the alcohols, aldehydes and ketones, can also be used either singly or in combination with one another. The former is preferred.

Stoichiometric amounts of alcohol and aminating agent are required for the practice of this invention. However, for reasons of convenience and efficiency it is preferable to practice this invention with a stoichiometric excess of aminating agent to alcohol. Typically, a minimum aminating agent:alcohol mole ratio of about 1:1 and preferably of about 10:1 is employed. Practical considerations, such as economy, reaction equipment, etc., are the only limitations upon the maximum said ratio but these considerations prefer a mole ratio of about 200:1 and more preferably of about 100:1. The typical aminating agent:aldehyde, ketone or mixture mole ratios are generally the same as the here recited aminating agent:alcohol mole ratios.

The method of this invention generally employs hydrogen. The amount of hydrogen employed, if employed, can vary to convenience but a typical minimum hydrogen:alcohol mole ratio is at least about 0.1:1 and preferably is at least about 1:1. A typical maximum mole ratio is about 50:1 and preferably is about 20:1. Again, the typical hydrogen:aldehyde, ketone or mixture mole ratios are generally the same as the here recited hydrogen:alcohol mole ratios.

Although conventional reaction conditions can here be used, the superior catalytic activity of this invention's composition permits the ammonolytic process to proceed at lower temperatures and pressures. For example, this invention can be practiced at a temperature of at least about 75° C. although preferred reaction rates are obtained at a temperature of at least about 120° C. Pressures are of course dependent upon temperature but a minimum pressure of about 50 psi (345 kPa) can be used. A minimum pressure of about 500 psi (3450 kPa) is preferred, and a minimum pressure of about 1,000 psi (6900 kPa) is most preferred. Again, practical considerations are the only limitations upon the maximum temperature and pressure but a maximum temperature of about 400° C. and a maximum pressure of about 10,000 psi (69,000 kPa) are preferred. A more preferred maximum temperature is about 250° C. and a more preferred maximum pressure is about 3,000 psi (20,700 kPa).

The invention can be practiced on either a continuous or batch operation, in both the liquid and gas phases, and either neat or in the presence of an inert solvent. By "inert" is meant that the solvent is essentially nonreactive with the method reagents and products at the method conditions. Exemplary solvents include aliphatic and aromatic hydrocarbons, such as hexane, heptane, cyclohexane, benzene, toluene, xylene, etc.; and nonreactive tertiary amines, such as pyridine, picoline, lutadine, etc. Moreover, this method can be practiced in either the presence or absence of water, although if water is present, it is preferred that it is not present in amounts greater than about 50 weight percent of the alcohol, aldehyde, ketone or mixture.

Whether the amines produced by this invention are primary, secondary, or tertiary depends not only upon the aminating agent employed, as earlier noted, but also upon the particular method conditions employed. Short contact time, e.g., between about 0.1 seconds and about 15 minutes, excess ammonia and low temperature and pressure generally favor the production of primary amines. As the aminating agent:alcohol, aldehyde, ketone or mixture mole ratio decreases and/or the temperature increases and/or the contact time increases, secondary and tertiary amines form a larger percentage of the method product. However, longer reaction time favors greater amination of the alcohol. Accordingly, by appropriate selection of aminating agent and method conditions, it is possible to influence the method product mix of primary, secondary and tertiary amines.

SPECIFIC EMBODIMENTS

The following examples and comparative experiments serve to illustrate certain specific embodiments of this invention. Unless otherwise noted, all parts and percentages are by weight.

General Procedures

A. Catalyst Preparation—Molten Salt Impregnation

A support material (100 g) is added to a molten mixture of metal salts at 90° C. The mixture is stirred occasionally over a period of 20 hours. The temperature is then raised over a 4-hour period to 300° C.–400° C. in intervals of 50° C. to dry and decompose the metal salts. A reduction is performed using a mixture of $H_2$ in $N_2$ starting at 100° C. with the temperature slowly increasing to 300° C.–400° C. over 6 hours. The resulting catalyst is recovered and is protected from contact with air.

B. Comparative Catalyst Preparation—Aqueous Impregnation

A support material (50 g) is added to a beaker. A solution of 40 ml of 2B ethanol (ethanol denatured with benzene) and 50 ml of deionized water is added to the beaker. A cobalt solution is prepared using 66 g of $Co(NO_3)_2.6H_2O$ and 300 ml of deionized water. A copper solution is prepared from 7.6 g of $Cu(NO_3)_2.3H_2O$ and 200 ml of deionized water. A rhenium solution is prepared from 2 g of $NH_4ReO_4$ and 25 ml of deionized water. The appropriate solutions are added to the beaker and the contents are stirred for 30 minutes. The beaker is allowed to sit overnight, and is evaporated to dryness in a vacuum evaporator. The dried solid material is heated in air in an oven at 80° C. for 2 hours, and is then calcined at 300° C. for 3 hours, and is reduced in $H_2$ at 175° C. for 3 hours.

COMPARATIVE EXPERIMENT 1

The general aqueous impregnation procedure is repeated with the following details and exceptions. The support is 38 g of Girdler T-869 silica, available from United Catalyst, Inc. The amounts of solutions added are: 36 ml of Co and 20 ml of Cu. Following the addition of the Co/Cu solution, a solution of 6 g of $(NH_4)_2CO_3.H_2O$ in 50 ml of deionized water is added slowly. The solution is evaporated using a vacuum evaporator, and the resulting material is dried in an oven in air overnight at 120° C. The material is calcined for 2 hours, and is reduced at 300° C.

COMPARATIVE EXPERIMENT 2

The general aqueous impregnation technique is repeated with the following details and exceptions. The support is wetted with 50 ml of 2B ethanol. The amounts of solutions are: 66 ml of Co; 42 ml of Cu; and 9.5 ml of Re.

COMPARATIVE EXPERIMENT 3

The procedure of Comparative Experiment 2 is repeated except that no Re is employed, and the reduction temperature is 400° C.

COMPARATIVE EXPERIMENT 4

The procedure of Comparative Experiment 2 is repeated with a different support.

COMPARATIVE EXPERIMENT 5

The general molten salt impregnation procedure is employed using 280 g of $Ni(NO_3)_2.6H_2O$.

COMPARATIVE EXPERIMENT 6

$Al_2O_3$ (100 g) is dried at 120° C., and then is added to 80 ml of a NaOH solution which is prepared using 12 g of NaOH and 80 ml of deionized water. The solids are filtered and dried at 120° C. The resulting modified support is impregnated with 140 g of $Ni(NO_3)_2.6H_2O$ at 80° C., is calcined at 125° C. in air, and is then heated, at a rate such that the temperature increases 35° C. per hour, to 400° C. and is held at 400° C. for 4 hours. The catalyst is reduced with $H_2$ at an initial temperature of 150° C. and the temperature is raised 50° C./hour to 450° C.

C. Reaction Procedure

Five grams of the reduced catalyst is mixed, in the absence of air, with 25.5 g of monoethanolamine and 5.0 g of water in a 300-ml reaction vessel. Then, 70 g of liquid $NH_3$ and 350 psig $H_2$ are added under a nitrogen atmosphere. The reaction vessel is heated to 175° C. in a rocking furnace for 6 hours. Then the vessel is quenched in a water bath. Excess $NH_3$ and $H_2$ are vented, then the reaction products are analyzed by vapor phase chromatographic methods. The results are listed in the following table.

| Run | Cu Salt[1] (g) | Co Salt[2] (g) | 3d Salt[3] | Support | % MEA Conversion | EDA:Piperazine |
|---|---|---|---|---|---|---|
| Ex. 1 | 100 | 100 | — | $SiO_2$ | 28 | 9 |
| C.E. 1 | .75 M | .75 M | — | $SiO_2$ | 20 | 8 |
| Ex. 2 | 140 | 140 | Re | $SiO_2$ | 35 | 9 |
| C.E. 2 | .75 M | .75 M | Re | $SiO_2$ | 9 | 6 |
| Ex. 3 | 100 | 100 | — | $TiO_2$ | 39 | 11 |

-continued

| Run | Cu Salt[1] (g) | Co Salt[2] (g) | 3d Salt[3] | Support | % MEA Conversion | EDA:Piperazine |
|---|---|---|---|---|---|---|
| Ex. 4 | 100 | 100 | Re | $TiO_2$ | 42 | 8 |
| Ex. 5 | 70 | 70 | — | $Al_2O_3$ | 35 | 6 |
| Ex. 6 | 140 | 140 | Re | $Al_2O_3$ | 57 | 7 |
| C.E. 3 | .75 M | .75 M | — | $TiO_2$ | 13 | * |
| C.E. 4 | .75 M | .75 M | Re | $TiO_2$ | 4 | * |
| C.E. 5 | | | 280 g[4] | $SiO_2$ | 23 | 8 |
| C.E. 6 | | | 140 g[4] | $Al_2O_3$ | 19 | 7 |

[1] $Cu(NO_3)_2 \cdot 2.5H_2O$
[2] $Co(NO_3)_2 \cdot 6H_2O$
[3] Re, when present, is 0.5 percent of the catalyst
[4] $Ni(NO_3)_2 \cdot 6H_2O$
*Piperazine not detected

What is claimed is:

1. In a method of producing amines wherein at reactive conditions at least one alcohol, ketone, or aldehyde is contacted with an aminating agent in the presence of a supported ammonolytic catalyst consisting essentially of cobalt, copper and up to about 20 percent of a promoter metal, improvement comprising using as the catalyst a supported ammonolytic catalyst consisting essentially of cobalt, copper and up to about 20 percent of a promoter metal prepared by the molten salt impregnation technique.

2. A process of claim 1 wherein the catalytic metal component consisting essentially of from about 1 to about 95 percent cobalt and from about 8 to about 95 percent copper and up to about 20 percent of at least one promoter metal selected from the group consisting of Fe, Zn, Zr, Re, Cr and mixtures thereof.

3. A process of claim 1 wherein the support is a refractory metal oxide.

4. A process of claim 3 wherein the support is silica or alumina.

5. A process of claim 2 wherein the catalytic metal component consisting essentially of from about 5 to about 80 percent cobalt, from about 15 to about 60 percent copper, and from about 1 to about 15 percent of the additional promoter metal.

6. A process of claim 5 wherein the catalytic metal consisting essentially of from about 6 to about 70 percent cobalt, from about 20 to about 50 percent copper, and from about 4 to about 10 percent of the additional promoter metal.

7. A process of claim 1 wherein the catalyst is substantially free of nickel.

8. A process of claim 2 wherein the additional catalytic metal is iron, zinc, or zirconium.

9. A process of claim 8 wherein the additional metal is zirconium.

* * * * *